United States Patent [19]

Kaufman

[11] Patent Number: 5,238,820

[45] Date of Patent: Aug. 24, 1993

[54] MULTIPLY-AMPLIFIABLE VECTORS FOR HIGH LEVEL EXPRESSION OF EXOGENUOS DNA

[75] Inventor: Randal J. Kaufman, Boston, Mass.

[73] Assignee: Genetics Institute, Inc., Cambridge, Mass.

[21] Appl. No.: 421,228

[22] Filed: Oct. 13, 1989

Related U.S. Application Data

[63] Continuation-in-part of Ser. No. 919,801, Oct. 23, 1986, abandoned, which is a continuation-in-part of Ser. No. 795,379, Nov. 5, 1985, abandoned.

[51] Int. Cl.$^5$ .................... C12P 21/00; C12N 15/85; C12N 5/10
[52] U.S. Cl. .................... 435/69.1; 435/172.3; 435/240.2; 435/320.1
[58] Field of Search .................... 435/69.1, 70.1, 91, 435/172.1, 172.3, 240.2, 252.3, 320.1; 536/27; 935/6, 8, 9, 10, 22, 33, 34, 59, 60, 61, 66, 70

[56] References Cited

U.S. PATENT DOCUMENTS

| | | | |
|---|---|---|---|
| 4,396,601 | 8/1983 | Salser | 424/94.5 |
| 4,399,216 | 8/1983 | Axel | 435/6 |
| 4,634,665 | 8/1987 | Axel | 435/69.1 |
| 4,656,134 | 4/1987 | Ringold | 435/91 |
| 4,713,339 | 12/1987 | Levinson et al. | 435/240.2 |
| 4,740,461 | 4/1988 | Kaufman | 435/69.1 |

FOREIGN PATENT DOCUMENTS

WO83/03259 9/1983 PCT Int'l Appl. .
WO86/06409 11/1986 PCT Int'l Appl. .

OTHER PUBLICATIONS

Yeung et al., 1985, J. Biol. Chem., 260(18): 10299–10307.
Yeung, C. et al., J. Biol. Chem. 258:8338-8345 (1983).
Ingolia, D. et al., J. of Biol. Chem. 260:13261–13267 (1985).
Hunt, S. et al., J. of Biol. Chem. 258:13185-13192 (1983).
Fernandez-Mejia, C. et al., J. of Cell. Phys. 120:321-328 (1984).
Stark, G., Ann. Rev. Biochem. 53:447–491 (1984).
Gething, et al., Nature 293: 620-25 (1981).
Hartman, et al., PNAS USA 79: 233-37 (1982).
Kaufman, et al., J. Mol. Biol. 159: 601-21 (1982).
Kaufman, et al., PNAS U.S.A. 83: 3136-40 (1986).
Kim, et al., Cell 42: 129-38 (1985).
Lau, et al., Chem. Abstracts 102: 18671d (1985).
McIvor, et al., Annals NY Acad Sci 451: 245-49 (1984).
Milbrandt, et al., Mol and Cell. Biol. 3: 1274-82 (1983).
Pfarr, et al., DNA 4(6): 461-67 (1985).
Rowland, et al., Archives of Biochem. and Biophysics 239: 396–403 (Jun. 1985).
Schimke, Cell 37: 705-13 (Jul. 1984).
Stark, Ann. Rev. Biochem. 53: 447-91 (1984).
Yeung, et l., J. Biol. Chem. 258: 15179-85 (1983).

Primary Examiner—Richard A. Schwartz
Assistant Examiner—Nancy T. Vogel
Attorney, Agent, or Firm—Patricia A. McDaniels; Bruce M. Eisen; David L. Bernstein

[57] ABSTRACT

A transformation vector containing a heterologous product gene and two or more different heterologous selectable amplifiable marker genes is described. Preferably, the marker genes form a polycistronic transcription unit. Also described is a method for obtaining high level expression of a desired protein by culturing eukaryotic cells containing the vectors of the invention.

10 Claims, No Drawings

MULTIPLY-AMPLIFIABLE VECTORS FOR HIGH LEVEL EXPRESSION OF EXOGENUOS DNA

This application is a continuation-in-part of application Ser. No. 919,801, filed Oct. 23, 1986, now abandoned, which is a continuation-in-part of application Ser. No. 795,379, filed Nov. 5, 1985, now abandoned.

This invention relates to a method and unique expression vectors that use two or more different heterologous selectable amplifiable genes to obtain high expression levels of DNA coding for heterologous protein or polypeptide in a eukaryotic host cell.

BACKGROUND

Transformation is a commonly-employed genetic engineering procedure in which new genetic material is acquired by eukaryotic or procaryotic cells by the incorporation of exogenous DNA sequences coding for a desired protein or polypeptide. Ordinarily, the number of cells in a population undergoing transformation which actually incorporate the exogenous DNA is quite low. The problem of low transformation of the exogenous DNA can be obviated by transforming the host cell with a selection marker, (i.e. DNA encoding an easily-identifiable marker, such as resistance to an antibiotic) in addition to the exogenous DNA sequence. Upon transformation, the cell population is examined for the presence of the marker. Depending upon whether and how closely the selection marker is linked to the exogenous protein-encoding DNA, cells carrying the selection marker will also contain the exogenous DNA. Those cells which have successfully incorporated the marker DNA will exhibit the marker identity (e.g. survival in media containing the antibiotic) and those cells which have failed to incorporate the marker will not exhibit the marker feature (e.g. they will die upon exposure to the antibiotic).

The level of exogenous protein expressed by the transformed cells can also be substantially increased where a DNA encoding an amplifiable gene as well as a selectable marker is included in the transformation process. Amplification of a gene involves exposing the transformed cell to environmental pressure sufficient to require the cell to produce more copies of the amplifiable gene for survival.

The marker/amplification system most extensively used employs the gene for dihydrofolate reductase (DHFR), a fairly ubiquitous gene found in many cell lines. Exposing a cell transformed with DHFR-encoding DNA to cytotoxic concentrations of methotrexate (MTX) encourages the cell to amplify DHFR to survive. Cells which survive the MTX selection procedure have many copies of the DNA encoding DHFR. When the DHFR gene is on a plasmid containing a DNA sequence for another gene, that gene generally becomes amplified as well. Thus when transforming a cell with a vector containing a DHFR gene and an exogenous gene, the DHFR behaves as a selectable marker to enable the identification of those cells which have incorporated the vector from those cells which have not. The DHFR itself is also capable of being amplified and consequently amplifies the exogenous DNA. In practice, the DHFR system has demonstrated general utility only with one cell line, a Chinese hamster ovary line which is deficient in DHFR (CHO DHFR-). [Urlaub et al., *Proc. Natl. Acad. Sci. U.S.A.,* 77:4216-4220 (1982)]. Some efforts have been reported to overcome this limitation. [See e.g., Simonson, C. C. et al., *Proc. Natl. Acad. Sci, U.S.A.,* 80:2495-99, (1983), Murray, M. J. et al., *Mol. Cell, Biol.* 3:32-43 (1983)]. However, obtaining the optimal conditions necessary for expression of exogenous proteins has yet proven difficult.

Other selectable, amplifiable markers include adenosine deaminase ("ADA") [See, e.g., R. J. Kaufman et al., *Proc. Nat'l. Acad. Sci. USA,* 83:3136-3140 (1986) and those listed in G. R. Stark et al., "Gene Amplification" in Ann. Rev. *Biochem,* 53: 447-491 (1984). Other systems for amplifying and expressing heterologous DNA in a variety of different cell lines remain an unfulfilled need in the art.

SUMMARY OF THE INVENTION

As one aspect of the present invention, a method has been discovered in which a desired heterologous protein or polypeptide can be produced in large quantities by transforming eukaryotic cells with vectors containing two or more different heterologous selectable and amplifiable marker genes, as well as a gene coding for the desired protein. According to this method, the transformed cells are first grown under suitable conditions for selecting and amplifying one heterologous selectable amplifiable marker gene, thereby increasing the copy number of the desired protein gene. The transformed cells are then grown under suitable conditions for selecting and amplifying the second heterologous selectable amplifiable marker gene, thereby further increasing the number of copies of the desired protein gene. This process is repeated for each additional selectable marker that may be present. The transformed cells contain high copy numbers of the desired heterologous protein gene due to this multiple amplification afforded by the two or more different heterologous selectable amplifiable marker genes. These transformed cells are then grown under conditions in which the desired protein is expressed. Thus, the invention comprises methods for serially amplifying two or more different heterologous selectable amplifiable marker genes to obtain cells having high copy numbers of the desired heterologous product gene.

In another aspect, the present invention provides eukaryotic cells containing high copy numbers of a heterologous gene coding for a desired protein and two or more different heterologous selectable amplifiable marker genes for use in the method. In yet another aspect, the invention provides expression vectors containing two or more different heterologous selectable amplifiable marker genes and a heterologous protein gene for use in transforming cells according to the method.

In one preferred embodiment, the invention provides a vector containing a polycistronic transcription unit composed of DNA coding for two or more different heterologous selectable amplifiable marker genes. In another embodiment, two or more different heterologous protein genes can be independently amplified in the same host cell using two or more different heterologous selectable amplifiable marker genes.

DETAILED DESCRIPTION OF THE INVENTION

In accordance with the present invention, eukaryotic cells capable of expressing high levels of a desired heterologous protein are obtained by transformation with a vector containing at least two heterologous selectable amplifiable marker genes in addition to the desired protein gene.

Initially, the transformed cell line is selected for one marker gene. Selection transformants then are screened for presence of the desired protein gene in the cell DNA, for example, ligation of the desired protein gene into their chromosomes, or for expression of the protein itself. The former can be accomplished using Southern blot analysis, the latter by standard immunological or enzymatic assays. Once the transformants have been identified, expression of the protein gene is amplified by subculturing in the presence of a suitable selection agent for the first marker gene. When that marker gene is amplified in copy number, it provides an increase in copy number of the desired protein gene. Cells having high copy numbers of the first marker gene and protein gene by virtue of this first amplification process can be further selected for a second marker gene. The second marker gene is amplified in copy number by subculturing in the presence of a suitable selection agent for the second marker gene, providing a further increase in copy number of the desired protein gene. Any other marker genes present can be similarly serially selected and then amplified in sequence to provide further increases in copy number of the desired product gene.

In one embodiment of the present invention, two or more different heterologous selectable amplifiable marker genes are transformed into a eukaryotic cell as a polycistronic transcription unit. A "transcription unit" defines a DNA sequence containing a gene coding for a desired protein, or a selection marker, or the like, under the control of a suitable promoter and having all the essential functions to enable expression. A "polycistronic transcription unit" is a transcription unit in which more than one gene is under the control of the same promoter. For example, the gene for one selection marker is inserted into the 5' untranslated region of the gene for a second selection marker. The gene for the second selection marker (which is in the 3' untranslated region of the gene for the first selection marker) is thereby expressed at a lower level than the gene for the first selection marker. This polycistronic transcription unit (or polycistronic selection unit) is thus doubly amplifiable.

When the polycistronic selection unit and a desired protein gene are inserted into a cell line, the cells are subjected to selection pressure for the first marker. The first marker gene and desired protein gene are amplified under suitable selection pressure. The second marker gene in the unit is consequently amplified at a low level. However, because it is expressed at a low level, the second marker gene can be selected and further amplified under different suitable selection pressure for the second marker, thereby further amplifying the copies of the desired protein gene.

In other embodiments of the present invention, the polycistronic transcription unit may be more than doubly amplifiable by providing more than two selection markers in a polycistronic transcription unit, as described above. Alternatively, more than one vector may be employed, each containing one or more selection markers thereon. In one preferred triply amplifiable selection system according to the present invention, two of the markers are inserted into the vector DNA as a polycistronic transcription unit and the third marker is inserted as a separate transcription unit in another vector.

When two marker genes are present, the amplification is performed as follows: (a) One or more cells from the transformant cell population that express the desired protein in a preferential fashion when compared to other cells in the population is selected. (b) The selected cell or cells is cultured to a subsequent cell population under conditions designed to select for a change in the expression of the phenotypic characteristic of the first marker gene. (c) One or more cells from the subsequent cell population that express the product in a preferential fashion when compared to other cells in the subsequent population is further selected. (d) This further selected cell or cells is then cultured to a subsequent cell population under conditions designed to select for a change in the expression of the phenotypic characteristic of the second marker gene. (e) One or more cells from the cell population that express the product in a preferential fashion when compared to other cells in the population is selected. Steps (b) and (d) advantageously are conducted with plurality of the step (a) or (c) clones, respectively. Where more than two marker genes are present, steps (c), (d) and (e) may be repeated, selecting for each additional marker gene present.

The cell to be transformed may be any eucaryotic cell, including yeast protoplasts, and various bacterial cells, but is preferably a nonfungal cell and most preferably, is a stable mammalian cell line. Useful in the practice of this invention are HeLa cells, melanoma cell lines such as the Bowes cell line, mouse L cells, mouse fibroblasts, mouse NIH 3T3 cells, and the like. Cell lines that are known to stably integrate heterologous DNA, such as selection genes and product genes, into their chromosomal DNA are also desirable, e.g., Chinese hamster ovary (CHO) cell lines, human hepatoma Hep G2 cell lines and mouse myeloma cell lines, depending upon the other requirements placed upon the cell line.

Any selectable amplifiable marker gene can be used in the practice of the present invention. Many such genes are known to those of skill in the art. [See, Stark et al., supra.]Exemplary marker genes for use in the invention include ADA and DHFR. The selectable marker may also be a gene producing a cell surface antigen which is detected by reaction with an antibody therefor, the antibody having a detectable label thereon, e.g., a fluorescent tag. Examples of surface antigens useful for this approach include the influenza virus hemaglutinin protein [M. J. Gething et al., *Nature* 300:598 (1982)], the T-cell antigen leu-2 [P. Kavathas et al., *Proc. Nat. Acad. Sci.* 80:524 (1983)], and the transferrin receptor [L. C. Kuhn et al. *Cell,* 37:95 (1984)].

The particular marker genes used together in the vectors, transformed cells and method of the invention must be independently selectable and amplifiable. The conditions used to place selection pressure on the cell line must select only one amplifiable marker gene at a time and have no substantial selection effect on any other amplifiable marker genes used in the method. The specific selection method to be used can be determined by the person of ordinary skill in the art, depending on the particular combination of marker genes employed. Such selection methods, per se, do not form part of the present invention. In some embodiments of the present invention the selection method may involve physical sorting techniques, rather than chemical selection procedures, such as exposure to increasing concentration of MTX.

The desired protein genes which can be used in the method and vectors of the present invention are essentially unlimited. Genes coding for substances that are proteins or that can be made by protein based reaction, such as enzyme conversions, are suitable. Genes for proteins that may adversely affect the whole cell by synthesizing toxins or hydrolyzing host protein, e.g., some enzymes from procaryotic or lower eucariotic sources, may be employed with qualifications such as providing antitoxins in the culture medium or by selecting lower expression levels than would otherwise be optimum. Genes for proteins that are enzymes having activities that are found in the cells of higher animals, such as mammals or vertebrates, are the genes of most interest herein.

Vector(s) useful in the practice of this invention may contain a plurality of discrete protein genes. Additionally, such vectors will contain one or more elements such as enhancers, promoters, introns, accessory DNA, a polyadenylation site and three prime non-coding regions. [See S. C. Clark et al., *Proc. Natl. Acad. Sci USA,* 81:2541-2547 (1984); see also R. J. Kaufman, *Proc. Natl. Acad. Sci. USA* 82:689-693 (1985)]. These may be obtained from natural sources or synthesized by known procedures. Basically, if the components found in DNA are available in large quantity, e.g., components such as viral functions, or if they are to be synthesized, e.g., polyadenylation sites, large quantities of vectors may be obtained with appropriate use of restriction enzymes by simply culturing the source organism, digesting its DNA with an appropriate endonuclease, separating the DNA fragments and identifying the DNA containing the element of interest and recovering the same.

To most effectively obtain coamplification of marker and desired protein genes, the use of linked vectors in which the marker and product genes are covalently bound is preferred. The coding strands of the marker gene transcription unit and product gene transcription unit are preferably joined by directly ligating the product stop codon adjacent to the marker gene start codon. The genes may be ligated in the same DNA strand through an oligodeoxyribonucleotide bridge. The bridge should be free of termination or start codons, and of palindromes to reduce the probability of forming RNA hairpin loops. Linked vectors may be in the form of a polycistronic transcription unit in which the 3' end of one gene is linked to the 5' end of the second gene under control of the same promoter.

Transformation with unlinked vectors (one vector containing the marker genes and another vector containing the desired exogenous product gene) can also be employed and accomplished simultaneously. [See, e.g. U.S. Pat. No. 4,399,216]. Methods for facilitating cellular uptake of DNA are well known to those skilled in the art. Considerably better transformation efficiencies result from transformation with a molar excess of product gene to marker gene, preferably on the order of 10:1 or higher. The vectors for use in producing the cells or cell lines useful in the method of the present invention are preferably supercoiled, double-stranded circular constructs, the form in which vectors are obtained from the standard prokaryotic cloning procedure. However, the vectors may be linearized, i.e., covalently cleaved at one point, incidental to other steps such as ligation to genomic accessory DNA.

A variety of procedures and vector constructions can be used to practice the present invention and provide multiple amplification of a desired protein gene. Examples of such include:

(a) Vector I containing a Marker 1-Marker 2 polycistronic transcription unit linked to Vector II containing a desired protein transcription unit inserted into a cell under conditions favoring DNA uptake followed by sequential subculturing in the presence of suitable selection agents to obtain double amplification (i.e., amplification due to Marker 1 followed by amplification due to Marker 2).

(b) Vector I containing a Marker 1 transcription unit linked to Vector II containing a Desired Protein-Marker 2 polycistronic transcription unit inserted into a cell under conditions favoring DNA uptake followed by sequential subculturing in the presence of suitable selection agents to obtain double amplification.

(c) Vector I containing a Desired Protein-Marker 1-Marker 2 polycistronic transcription unit inserted into a cell under conditions favoring DNA uptake followed by sequential subculturing in the presence of suitable selection agents to obtain double amplification.

(d) Vector I containing a Desired Protein 1-Marker 1 polycistronic transcription unit linked to Vector II containing a Desired Protein 2-Marker 2 polycistronic transcription unit inserted into a cell under conditions favoring DNA uptake followed by sequential subculturing in the presence of suitable selection agents to obtain double amplification.

(e) Vector I containing a Desired Protein 1 transcription unit linked to Vector II containing a Marker 1 transcription unit inserted into cell 1 under conditions favoring DNA uptake; Vector III containing Desired Protein 2 transcription unit linked to Vector IV containing Marker 2 transcription unit inserted into cell 2 under conditions favoring DNA uptake, subculturing of cells 1 and 2 in the presence of suitable selection agents to obtain double amplification followed by fusion of cell 1 and cell 2 to obtain cell having Desired Protein 1, Desired Protein 2, Marker 1 and Marker 2 in the chromosomal DNA.

(f) Vector I containing a Desired Protein transcription unit linked with Vector II containing a Marker 1 transcription unit and Vector III containing a Marker 2 transcription unit inserted into a cell under conditions favoring DNA uptake followed by subculturing in the presence of suitable selection agents to provide double amplification.

(g) Vector I containing the Desired Protein transcription unit linked with a Marker I Marker II transcription unit and Vector II containing a Marker III transcription unit are transfected into cells and selection for Marker III is applied. Transformants are selected for increased Marker III expression then selection is changed to Marker I and cells exhibiting increased Marker I expression are obtained. Then selection is changed to Marker II to obtain cells which express increased amounts of Marker II. During this time, the levels of desired protein expressed increase proportionally to the gene copy number.

One example of a doubly amplifiable polycistronic selection unit is an adenosine deaminase-dihydrofolate reductase transcription unit (ADA-DHFR). An example of a triply amplifiable polycistronic selection unit employs the ADA gene, and the influenza virus hemaglutinin - dihydrofolate reductase (HA-DHFR) polycistronic transcription unit. The production of DHFR cDNA is well known to those skilled in the art and plasmids containing DHFR genes are widely known and available. The production of ADA and HA cDNA follows a procedure analogous to that for cloning any other gene. [See generally T. Maniatis et al., *Molecular Cloning A Laboratory Manual*, Cold Spring Harbor Laboratory (1982); see also J. Toole et al., *Nature* 312:342-347 (1984)]. Human and murine ADA cDNAs have been cloned and their sequences determined. [See S. H. Orkin et al., *Mol. Cell Biol.* 5:762-767 (1985); D. A. Wiginton et al., *Nucl. Acids Res.* 12: 1015-1024 (1984); D. Valerio et al., *Gene*, 31: 147-153 (1984) and C. Yeung et al., *J. Biol. Chem.*, 258:15179-15185 (1983)]. Similarly the sequence for HA genes are known. See, e.g. Gething et al., supra. These cDNAs can be placed into mammalian expression vectors using techniques well known by those having ordinary skill in the art to create vectors useful in the method of the invention. [See R. J. Kaufman, *Proc. Natl. Acad. Sci. USA* 82:689-693 (1985); Maniatis et al., supra].

The following examples illustrate the several vectors for use in the method of the present invention.

EXAMPLE I

Construction of a Polycistronic ADA-DHFR Transcription Unit

Murine ADA cDNA, pADA5-29 [See Yeung et al., *J. Biol. Chem.*, 260: 10299-307 (1985)]was placed into a mammalian expression vector p90123B. p91023B is derived from plasmid pCSF-1 which was deposited on Jul. 2, 1984 with the American Type Culture Collection, 12301 Parklawn Drive, Rockville, Md. in *E. coli* MC1061 under ATCC deposit number 39754, by deleting the CSF gene therein with EcoRl digestion. This vector p91023B contains the adenovirus VA gene, the SV40 origin of replication including the 72 bp enhancer, the adenovirus major late promoter including the adenovirus tripartite leader and a 5' splice site, a 3' splice acceptor site, a murine DHFR cDNA gene under transcriptional control of the adenovirus promoter, the ADA insert, the DHFR insert, the SV40 early polyadenylation site and pBR322 sequences needed for propagation in *E. coli*. The 1056 nucleotide open reading frame in pADA5-29 (Yeung et al., at p. 10304) was excised by NcoI and EcoRl digestion. The ends were filled in using Klenow fragment of DNA polymerase 1 and blunt-end ligated into the EcoRl site of vector p91023B. The resultant vector, p9ADA5-29 contains the ADA insert between the 3' splice acceptor site and the DHFR gene. Vector p9ADA5-29, was used to transfect COS-1 cells using the DEAE-dextran procedure. [R. J. Kaufman, Proc. Natl. *Acad. Sci USA*, supra]. The transfected cells underwent zymogram analysis which indicated that the cells produced authentic mouse ADA at high levels.

A similar vector containing an ADA-DHFR transcription unit can be obtained by removing the VWF gene sequence from plasmid pMT2-ADA-VWF by EcoRI digestion and religating the two ends of the plasmid. pMT2-ADA-VWF was deposited with the American Type Culture Collection, 12301 Parklawn Drive, Rockville, Md. on Jul. 31, 1986 under accession number 67172. The resulting plasmid pMT2ADA is similar to p91023B and includes the adenovirus VA genes, the SV40 origin of replication including the 72 bp enhancer, the adenovirus major late promoter including a 5' splice site, the majority of the adenovirus tripartite leader sequence present on adenovirus late mRNA's, a 3' splice acceptor site, the ADA insert, the DHFR insert, the SV40 early polyadenylation site and pBR322 sequences needed for propagation in *E. coli*. However, this plasmid contains the ampicillin resistance gene in place of the tetracycline resistance gene in p91023B.

Cells into which the ADA-DHFR transcription unit and a desired protein gene are transformed are first selected for the ADA marker gene using, e.g. (R) deoxycoformycin (dCF) as a selection agent, providing up to 100 fold or more amplification of the desired protein gene. The cells, after having been selected for ADA, are then further selected for DHFR using methotrexate (MTX) as a selection agent, providing up to an additional 10 fold or more amplification of the desired protein gene.

Other methods for selecting for increased ADA expression are summarized in Kaufman et al., supra. and references cited therein, but those skilled in the art can adapt those and other methods in order to select for cells containing heterologous ADA.

(a) One such ADA selection method involves the use of adenosine analogues. Cells can be selected for resistance to cytotoxic adenosine analogues 9-$\beta$-D-arabinofuranosyl adenine (Ara-A) or 9-$\beta$-D-xylofuranosyl adenine (Xyl-A). Multiple step selection in either Ara-A or Xyl-A results in cell populations with increased ADA activity. [See C. Yeung, et al., *J. Biol. Chem.*, 258: 8330-8337 (1983)]. ADA has the ability to catalyze the irreversible conversion of these adenine analogues to their respective inosine derivatives which are eventually detoxified by removal of the ribose by purine nucleoside phosphorylase to yield hypoxanthine. Because cells may become resistant to these analogues by loss of adenosine kinase activity, not all surviving cells will have increased levels of ADA. [V. L.Chan et al. *Somatic Cell Genet.* 7:147-160 (1981); Yeung, et al., supra.. However, the frequency of loss of adenosine kinase is usually low in cells which contain a diploid complement of the adenosine kinase gene.

(b) A selection protocol which selects for the presence of adenosine kinase [T. Chan et al., *Somatic Cell Genetics* 4: 1-12 (1978)] has been modified so that it can also be used to select for increased expression of ADA. [See C. Yeung et al., supra 15179-15185 (1983)]. In contrast to the first procedure, all surviving cells exhibit increased levels of ADA. Under this growth condition, cells are blocked in de novo AMP (adenosine monophosphate) biosynthesis by alanosine and require adenosine kinase to convert adenosine to AMP. Since adenosine depletes phosphoribosylpyrophosphate (PRPP) which results in the inhibition of endogenous pyrimidine synthesis, the medium is supplemented with uridine. [See H. Green et al., *Science* 182: 836-837 (1973); K. Ishii et al., *Cell Sci* 13: 429-439 (1973)]. However, when the adenosine concentration is increased 11-fold [hereinafter 11-AAU (adenosine, alanosine, uridine) selection]the high concentrations of adenosine become cytotoxic and ADA is required to alleviate the toxicity. [See I. H. Fox et al., *Ann Rev Biochem* 47: 655-686 (1978)].

(c) Once functional ADA is required for cell growth, (R)-deoxycoformycin (dCF), an antibiotic demonstrated to be a tight binding transition-state analogue inhibitor of ADA (kd=$2.5 \times 10^{-12}$), can be used to select for amplification of the ADA gene. [See R. P. Agarwal et al., *Biochem. Pharmacol.* 26: 359-367 (1977); C. Frieden et al., *Biochem.* 19: 5303-5309 (1980)]. For the cell to survive in these systems, ADA is required in higher levels than most cells produce. Growth of cells in 11-AAU in the presence of sequentially increasing concentrations of dCF, selects cells which contain a high degree of ADA expressions as result of amplification of the ADA gene. [See C. Yeung, supra at 8338-8345 (1983)].

(d) Yet another selection method employs deoxyadenosine as a carbon source. Cells can also be made growth dependent on ADA activity by blocking purine de novo synthesis with azaserine and feeding cells 2-deoxyadenosine as a purine source. [See Fernandex-Mejia et al., *J. Cell Physio.* 120: 321-328 (1984)]. Deoxyadenosine is available as a general purine source only if converted to deoxyinosine by ADA. As as result, cells can be selected for increased ADA activity by growth in azaserine with increasing concentrations of dCF. The medium is supplemented with deoxycytidine. [See L. Thelander et al., *Ann. Rev. Biochem.* 48: 133-158 (1979)]. et al., *J. Biol. Chem.* 258: 13185-13192 (1983), utilizing adenosine as the sole carbon source. Under these conditions, dCF resistant variants of Novikoff rat hepatoma cells which require functional ADA, were isolated by growing adenosine kinase-deficient cells in a medium containing adenosine as the sole carbon source with stepwise increasing concentrations of dCF. This procedure yields cells which have amplified the ADA gene 320-fold. [See also, P. S. Hoffee et al., *Somatic Cell Genet.* 8: 13185-13192 (1983)].

DHFR deficient CHO cells, CHO DHFR−, (DUKXB11), were grown in an alpha media with 10 $\mu$g/ml of thymidine, deoxyadenosine and adenosine. Cells were transfected with p9ADA5-29 (25 $\mu$g $10^6$ cells) as described by R. J. Kaufman et al., *J. Mol. Biol.*, 150:601-621 (1982). Forty-eight hours post-transfection, cells were plated (3×$10^5$ cells/10 cm plate) into alpha media supplemented with 10 $\mu$g/ml thymidine, 10 $\mu$g/ml deoxyadenosine, 1 mM uridine, 1.0 mM adenosine and varying concentrations of dCF. Four plates at each dCF concentration level were prepared. To avoid detoxification of the cytological agents by the low levels of ADA endogenous to fetal calf serum, 10% fetal calf serum was added just prior to use of the media.

Transformants were amplified using the 11-AAU procedure in combination with increasing levels of dCF as described in C. Yeung et al., supra at 8338-8345, and excluding alanosine. Transformants were maintained in DMEM supplemented with 10% fetal calf serum (Grand Island Biological Company) and incubated at 37° C. The transformed CHO DHFR- cells were grown in in the 11-AU medium described above.

Six transformed colonies which were selected for by 11-AU selection at dCF concentrations of 0.03 and 0.1 $\mu$M were placed in the above described media. These cells were then exposed to 0.1 $\mu$M or 0.5$\mu$M of dCF respectively. Those cells not producing large amounts of ADA were killed. Once growth resumed for surviving cells, the cells were passaged several times at the same level of dCF. Then the dCF concentration was increased. Cells were exposed to dCF step-wise at levels of 0.03 $\mu$M, 0.1 $\mu$M, 0.5 $\mu$M, 1 $\mu$M, 5 $\mu$M, and 20 $\mu$M.

Cells to be analyzed were removed from drug selection for 1 week and fed with fresh DMEM plus 10% serum 24 hours before harvest. Cells were harvested by trypsintization, washed three items with Hank's balanced salt solution (without $Mg^{2+}$ and $Ca^{2+}$), and resuspended in twice their packed volume of homogenizing medium (10 mM Tris-HCl, pH 7.5, 1 mM A -mercaptoethanol, and 1 mM EDTA). The resuspended pellet was frozen at −20° C., thawed and homogenized using a motorized Teflon homogenizer. The samples were centrifuged twice at 15,000×g for 30 minutes to remove debris. The supernatants (containing ~1 mg of protein/ml) were applied directly to starch gels. Electrophoresis was conducted at 4° C. using 200 V for 16 hours or 400 V for 5 hours. Following electrophoresis, the starch gel was sliced into replica sheets of approximately 1 mm thickness and histo-chemically stained for adenosine deaminase activity as described in J. M. Sicilano et al., *Chromatographic and Electrophoretic Techniques* (I. Smith, ed.) 4th Ed., vol 2, pp. 185-209 Wm. Heinemann Medical Books Ltd., London (1976); and H. Harris et al., *Handbook of Enzyme Electrophoresis in Human Genetics,* North/Howland, Oxford (1976).

This treatment resulted in an amplification for the transformants selected at 0.1 $\mu$M dCF of about 10-times and for the cells selected at 0.03 $\mu$M dCF of about 50-times. Further amplification is obtained by continuing to apply selection pressure on surviving cells with step-wise increments of dCF as described above.

EXAMPLE II

Expression of DHFR from the Polycistronic ADA-DHFR Transcript

The ADA-DHFR expression plasmid p9ADA5-29 contains an intact DHFR coding region in the 3' noncoding region of the ADA gene. To monitor DHFR expression from this polycistronic mRNA, the plating efficiency of the DHFR deficient CHO cells which contained highly amplified copies of the ADA-DHFR cDNA gene (p9ADA5-29) was determined in the presence of alpha media lacking nucleosides, which selects for low levels of DHFR expression. [See Kaufman and Sharp, *J. Mol. Biol.,* 150:601-621 (1982)], and in the presence of increasing concentrations of MTX. The plating efficiency of the CHO amplified transformants demonstrated significant growth in concentrations of MTX up to 0.2 $\mu$M. This result demonstrated a significant level of DHFR expression from the ADA-DHFR expression vector in the absence of any direct selection for DHFR expression.

Expression of DHFR was directly demonstrated by $^{35}S$ methionine radiolabelling and immunoprecipitation with a murine DHFR specific antibody. A band the appropriate weight for authentic murine DHFR was detected. Only a single DHFR mRNA species was observed in the amplified cells and the size of that species was identical to the ADA mRNA species. This observation demonstrated that DHFR expression was derived from the polycistronic ADA-DHFR transcript.

The plating efficiency for the original ADA transformant in 0.1 $\mu$M dCF and the amplified transformant in 100 $\mu$M dCF were determined by plating 200 and 2000 cells per 10 cm dish in increasing concentrations of MTX. Colonies were stained and counted 12 days after plating. Based on values expressed as a percent of the control plating efficiency, the dCF resistant line (the amplified transformant) in alpha media reflects the significantly greater ability of these cells to grow better in the absence of 11-AU with dCF selection.

The level of DHFR expression can be quantitated by monitoring the ability of cells to grow in various concentrations of MTX. The degree of MTX resistance is generally directly related to the level of DHFR expression [Alt et al., *J. Biol. Chem.* 252:1357-1370 (1978)]. Upon comparison of the amount of ADA expression (approximately 3% of the cellular protein determined from analysis of $^{35}$S-labeled cell extracts) to the amount of DHFR expression (approximately 0.2% of the cellular protein) determined from the level of MTX resistance (0.02 mM), the level of DHFR translation from the polycistronic transcript was calculated to be at least 10-fold lower than the level of ADA translation.

EXAMPLE III

Cotransformation and Coamplification

To illustrate the cotransformation and coamplification of a desired polypeptide utilizing a doubly-amplifiable vector system of the present invention, a p91023B derivative containing the sequence for CSF-1 was employed. One skilled in the art will acknowledge that any sequence coding for another selected polypeptide may be inserted into an analogous vector in an analogous manner by known procedures.

Plasmid p9ADA5-29, described in Example I, is mixed with pCSF-1 (ATCC 39754), which contains a DNA sequence coding for CSF-1. Specifically, 50 µg pCSF-1 is mixed with 0.5 µg p9ADA5-29 and precipitated by the addition of NaOAc (pH 4.5) to 0.3M and 2.5 vols. of ethanol. Precipitated DNA is allowed to air dry, then is resuspended in 2X HEBSS (0.5 ml) [Chu et al., *Gene* 13:197–202 (1981)]and mixed vigorously with 0.25M $CaCl_2$ (0.5 ml) as described in R. J. Kaufman et al., *J. Mol. Biol.*, supra. The calcium-phosphate-DNA precipitate is allowed to sit 30 minutes at room temperature, and applied to CHO DUKX-B1 cells [Chasin, et al., *Proc. Natl. Acad. Sci. USA* 77:4216–4220 (1981)]. The growth and maintenance of these cells has been described in Kaufman et al., *J. Mol. Biol.*, supra and Chasin et al., supra.

The DUKX-B1 cells are subcultured at $5 \times 10^5/10$ cm dish for 24 hours prior to transfection. The media is removed, and the DNA-calcium phosphate precipitate is added to the monolayer. After 30 minutes incubation at room temperature, 5 ml of alpha-media (Flow) with 10% fetal calf serum is applied and the cells are incubated at 37° C. for 4.5 hours. The media is then removed from the monolayer of cells, 2 ml of alpha-media (Flow) containing 10% glycerol is added for 3 minutes at room temperature (24° C.) and then removed and the cells are rinsed and fed with alpha-media containing 10% fetal calf serum, 10 µg/ml each of thymidine, adenosine, deoxyadenosine, penicillin and streptomycin. Two days later the cells are subcultured 1:15 in the selection media as described above.

Colonies will appear 10–12 days after subculturing into selective media. After CSF-1 expression has been maximized by amplification under selective pressure for the first selection marker ADA, the clones are propagated under selective conditions to increase expression of the second marker DHFR gene and CSF-1, i.e. increasing concentrations of MTX.

Two schemes for selection and amplification can be followed. In the first scheme single independent cloned transformants are isolated on the basis of uptake of the exogenous ADA DNA and subsequently each clone is propagated under conditions to increase expression of the CSF-1 gene i.e., growth in increasing concentrations of dCF. Each clone is then propagated under selective pressure for DHFR using increasing concentrations of MTX to maximize expression of the CSF-1. In the second scheme pools of multiple independent transformants are isolated on the basis of uptake of the exogenous ADA DNA and are propagated under conditions to increase expression of the CSF-1 gene, i.e., growth in increasing concentrations of dCF. Then individual clones are isolated from the mass selected population and analyzed for expression of the CSF-1. Those clones exhibiting highest levels of CSF-1 expression are grown again under conditions to further increase product expression (i.e., growth in increasing concentrations of dCF in the culture media.)

Individual clones are assayed for expression of the CSF-1. Those clones exhibiting highest levels of CSF-1 expression are propagated under selective pressure for DHFR using increasing concentrations of MTX to maximize expression of CSF-1.

EXAMPLE IV

Triply Amplifiable Vector System

To illustrate the cotransformation and coamplification of a desired polypeptide utilizing a multiply-amplifiable vector system of the present invention, a plasmid containing the sequence for Von Willebrand Factor was employed. One skilled in the art will acknowledge that any sequence coding for another selected polypeptide may be inserted into an analogous vector in an analogous manner by known procedures.

A triply amplifiable vector system according to the present invention was constructed employing the genes for DHFR, ADA and the influenza virus hemaglutinin (HA). The influenza virus hemaglutinin clone, P5, was obtained from John Skehel of Mill Hill, London England, and encodes a complete copy of the influenza A/X31 HA gene. P5 contains the HA gene blunt-ended into a filled Sal I site of small bacteriophage M13mp8. The orientation of the gene is such that its 3' end is nearest the Bam HI site in the polylinker region of M13mp8. This DNA is digested with Sma I (which digests at the 5' end in the polylinker) and Pst I adapters are applied. The resultant DNA is digested with Pst I and the HA gene fragment is isolated by gel electrophoresis and inserted into the Pst I site of plasmid pMT2. pMT2 is similar to p91023B except that it contains the ampicillin resistance gene in place of the tetracycline resistance gene. The resultant plasmid pMT2HA expresses a polycistronic HA-DHFR transcript. pMT2HA was deposited with the American Type Culture Collection, 12301 Parklawn Drive, Rockville, Md. under ATCC accession no. 67239 on Oct. 21, 1986.

This plasmid is mixed with an equal amount of pMT2-ADA-VWF (ATCC 67172), which contains an ADA transcription unit and a VWF gene. pMT2-ADA-VWF and pMT2HA are transfected by calcium phosphate coprecipitation into CHO DHFR deficient DUKX-B11 cells. The cells are selected for the presence of ADA as described above. The transformants are then pooled and stained with a murine monoclonal antibody, obtained by standard procedures, directed towards HA and secondary fluoresceinated antibody (goat anti-mouse IgG) obtained commercially from Becton Dickinson. The brightly staining cells (10%) are isolated with a fluorescence activated cell sorter (See P. Kavathas, supra.) The sterilely sorted cells are propagated for three weeks and the staining and sorting procedure is repeated. The final sorted cells are grown in the presence of alpha media lacking nucleotides which selects for the presence of DHFR. Then methotrexate is applied to further amplify the gene copy number. Other vectors containing ADA transcription units may be used in place of pMT2-ADA-VWF. One such vector is pSV2ADA [See, Orkin et al., supra]. Also, EcoRI digestion of pMT2-ADA-VWF to remove the VWF cDNA, will allow insertion of another protein gene into a polycistronic unit with ADA for amplification according to the above. The ADA sequence may be removed from pMT2-ADA-VWF as a 1.75 kb fragment by digestion with EcoRI and HpaI for insertion into another vector. Similarly, the HA gene may be removed from pMT2HA with Pst I for insertion into another vector according to the invention.

Those skilled in the art, upon consideration of this disclosure, may make numerous modifications and improvements thereto which are believed to be encompassed within the scope of the appended claims.

What is claimed is:

1. A transformed mammalian cell containing a selected heterologous protein gene and at least two different heterologous selectable amplifiable marker genes, wherein said protein gene and at least one of said marker genes form a polycistronic transcription unit.

2. A transformed mammalian cell according to claim 1, wherein said marker genes are selected from the group consisting of genese encoding adenosine deaminase, dihydrofolate reductase and influenze virus hemaglutinin.

3. A transformed mammalian cell according to claim 1, wherein said cell further contains multiple copies of said protein gene and said marker genes.

4. A transformed mammalian cell according to claim 1, wherein said transcription unit is an ADA-DHFR polycistronic transcription unit.

5. A method for obtaining expression of a desired protein comprising:
   (a) incorporating into mammalian cells a vector containing a heterologous gene encoding said protein and at least two different heterologous selectable amplifiable marker genes, wherein said heterologous gene and at least one heterologous marker gene form a polycistronic transcription unit;
   (b) selecting for transformants containing the protein gene and the marker genes;
   (c) amplifying by selective pressure for one of the marker genes and thereby amplifying the protein gene in the selected transformants to obtain first order amplified transformants;
   (d) further sequentially amplifying by selective pressure for each of the other marker genes present and thereby further amplifying the protein gene in the first order amplified transformants to obtain multiple order amplified transformants; and
   (e) expressing the amplified protein gene in the multiple order amplified transformants and recovering the desired protein.

6. The method according to claim 5, wherein said marker genes are selected from the group consisting of genes encoding adenosine deaminase, dihydrofolate reductase, and influenze virus hemaglutinin.

7. The method according to claim 5, wherein said transcription unit is an ADA-DHFR polycistronic transcription unit.

8. A transformation vector comprising a heterologous protein gene and at least two different heterologous selectable amplifiable marker genes, said heterologous protein gene and at least one heterologous marker gene forming a polycistronic transcription unit.

9. The transformation vector according to claim 8, wherein said marker genes are selected from the group consisting of genes encoding adenosine deaminase, dihydrofolate reductase, and influenze virus hemaglutinin.

10. The transformation vector according to claim 9, wherein one of said marker genes is expressed weakly and cannot be selected until amplified with another of said marker genes.

* * * * *